(12) United States Patent
Jalisi

(10) Patent No.: US 8,480,599 B2
(45) Date of Patent: *Jul. 9, 2013

(54) COMPOSITE RADIOPAQUE INTRACORPOREAL PRODUCT

(75) Inventor: Marc Mehrzad Jalisi, Temecula, CA (US)

(73) Assignee: Abbott Cardiovascular Systems, Inc., Santa Clara, CA (US)

( * ) Notice: Subject to any disclaimer, the term of this patent is extended or adjusted under 35 U.S.C. 154(b) by 203 days.

This patent is subject to a terminal disclaimer.

(21) Appl. No.: 13/046,436

(22) Filed: Mar. 11, 2011

(65) Prior Publication Data

US 2011/0166479 A1    Jul. 7, 2011

Related U.S. Application Data

(60) Continuation of application No. 11/928,275, filed on Oct. 30, 2007, now Pat. No. 7,905,003, which is a continuation of application No. 10/735,793, filed on Dec. 11, 2003, now Pat. No. 7,296,333, which is a division of application No. 09/995,196, filed on Nov. 26, 2001, now Pat. No. 6,679,853, which is a continuation of application No. 09/098,443, filed on Jun. 17, 1998, now Pat. No. 6,387,060.

(51) Int. Cl.
*A61M 25/09* (2006.01)

(52) U.S. Cl.
USPC .......................................... 600/585

(58) Field of Classification Search
USPC ............ 29/458, 456, 435, 505, 428; 600/585, 600/433–436
See application file for complete search history.

(56) References Cited

U.S. PATENT DOCUMENTS

| | | | |
|---|---|---|---|
| 4,538,622 | A | 9/1985 | Samson et al. |
| 4,748,986 | A | 6/1988 | Morrison et al. |
| 4,917,104 | A | 4/1990 | Rebell |
| 4,925,445 | A | 5/1990 | Sakamoto et al. |
| 5,005,596 | A | 4/1991 | Yamada |
| 5,061,273 | A | 10/1991 | Yock |
| 5,069,217 | A | 12/1991 | Fleischhacker, Jr. |
| 5,069,226 | A | 12/1991 | Yamauchi et al. |

(Continued)

FOREIGN PATENT DOCUMENTS

| | | |
|---|---|---|
| JP | 60168466 | 8/1985 |
| JP | 06/054912 | 1/1994 |

(Continued)

OTHER PUBLICATIONS

U.S. Appl. No. 09/098,443, Mail Date Jun.1 11, 1999, Office Action.

(Continued)

*Primary Examiner* — John C Hong
(74) *Attorney, Agent, or Firm* — Workman Nydegger; Ron Devore

(57) ABSTRACT

The invention is directed to a guidewire having a distal flexible member, such as a helical coil, which is formed with at least one highly radiopaque component and at least one high strength component. In a presently preferred embodiment, the highly radiopaque component is at least 10% and less than about 60% of the transverse cross-section of the flexible member, preferably at least 20% but less than 40%. The highly radiopaque component may be formed of radiopaque material such as platinum, gold, iridium and the like and the high strength component may be formed of a material such as tantalum, stainless steel, NiTi alloys, Co—Cr—Mo alloys and the like.

9 Claims, 2 Drawing Sheets

U.S. PATENT DOCUMENTS

| | | | |
|---|---|---|---|
| 5,135,503 A | 8/1992 | Abrams | |
| 5,144,959 A | 9/1992 | Gambale et al. | |
| 5,171,383 A | 12/1992 | Sagaye et al. | |
| 5,174,302 A | 12/1992 | Palmer | |
| 5,213,111 A | 5/1993 | Cook et al. | |
| 5,230,348 A | 7/1993 | Ishibe et al. | |
| 5,238,004 A | 8/1993 | Sahatjian et al. | |
| 5,253,653 A | 10/1993 | Daigle et al. | |
| 5,259,393 A | 11/1993 | Corso, Jr. et al. | |
| 5,341,818 A | 8/1994 | Abrams et al. | |
| 5,341,945 A | 8/1994 | Gibson | |
| 5,345,945 A | 9/1994 | Hodgson et al. | |
| 5,350,419 A | 9/1994 | Bendel et al. | |
| 5,372,144 A | 12/1994 | Mortier et al. | |
| 5,411,544 A | 5/1995 | Mar et al. | |
| 5,460,187 A | 10/1995 | Daigle et al. | |
| 5,476,505 A | 12/1995 | Limon | |
| 5,480,382 A | 1/1996 | Hammerslag et al. | |
| 5,506,059 A | 4/1996 | Robbins et al. | |
| 5,507,760 A | 4/1996 | Wynne et al. | |
| 5,514,154 A | 5/1996 | Lau et al. | |
| 5,516,336 A | 5/1996 | McInnes et al. | |
| 5,520,194 A | 5/1996 | Miyata et al. | |
| 5,588,443 A | 12/1996 | Davidson | |
| 5,607,463 A | 3/1997 | Schwartz et al. | |
| 5,628,787 A | 5/1997 | Mayer | |
| 5,630,840 A | 5/1997 | Mayer | |
| 5,630,843 A | 5/1997 | Rosenberg | |
| 5,636,641 A | 6/1997 | Fariabi | |
| 5,637,089 A | 6/1997 | Abrams et al. | |
| 5,645,082 A | 7/1997 | Sung et al. | |
| 5,647,127 A | 7/1997 | Miyata et al. | |
| 5,647,858 A | 7/1997 | Davidson | |
| 5,664,580 A | 9/1997 | Erickson et al. | |
| 5,695,111 A | 12/1997 | Nanis et al. | |
| 5,706,826 A | 1/1998 | Schwager | |
| 5,716,400 A | 2/1998 | Davidson | |
| 5,720,300 A | 2/1998 | Fagan et al. | |
| 5,720,775 A | 2/1998 | Larnard | |
| 5,724,989 A | 3/1998 | Dobson | |
| 5,725,570 A | 3/1998 | Heath | |
| 5,725,572 A | 3/1998 | Lam et al. | |
| 5,733,326 A | 3/1998 | Tomonto et al. | |
| 5,824,045 A | 10/1998 | Alt | |
| 5,824,056 A | 10/1998 | Rosenberg | |
| 5,824,077 A | 10/1998 | Mayer | |
| 5,843,166 A | 12/1998 | Lentz et al. | |
| 5,849,022 A | 12/1998 | Sakashita et al. | |
| 5,858,556 A | 1/1999 | Eckert et al. | |
| 5,871,850 A | 2/1999 | Moriguchi et al. | |
| 5,885,238 A | 3/1999 | Stevens et al. | |
| 5,891,191 A | 4/1999 | Stinson | |
| 6,030,333 A | 2/2000 | Sioshansi et al. | |
| 6,093,185 A | 7/2000 | Ellis et al. | |
| 6,099,457 A | 8/2000 | Good | |
| 6,129,735 A | 10/2000 | Okada et al. | |
| 6,132,388 A | 10/2000 | Fleming et al. | |
| 6,174,329 B1 | 1/2001 | Callol et al. | |
| 6,208,881 B1 | 3/2001 | Champeau | |
| 6,291,345 B1 | 9/2001 | Golecki et al. | |
| 6,329,069 B1 | 12/2001 | Azizi et al. | |
| 6,387,060 B1 | 5/2002 | Jalisi | |
| 6,520,923 B1 | 2/2003 | Jalisi | |
| 6,679,853 B1 | 1/2004 | Jalisi | |
| 7,294,356 B2 | 11/2007 | Jalisi | |
| 7,296,333 B2 | 11/2007 | Jalisi | |
| 7,905,003 B2 | 3/2011 | Jalisi | |
| 2002/0010505 A1 | 1/2002 | Richter | |
| 2008/0071194 A1 | 3/2008 | Jalisi | |

FOREIGN PATENT DOCUMENTS

| | | |
|---|---|---|
| JP | 09248703 | 9/1997 |
| WO | WO 97/00705 | 1/1997 |
| WO | WO 99/65558 | 12/1999 |

OTHER PUBLICATIONS

U.S. Appl. No. 09/098,443, Mail Date Jan. 10, 2000, Office Action.
U.S. Appl. No. 09/098,443, Mail Date Jul. 7, 2000, Office Action.
U.S. Appl. No. 09/098,443, Mail Date Aug. 17, 2000, Office Action.
U.S. Appl. No. 09/098,443, Mail Date Apr. 2, 2001, Office Action.
U.S. Appl. No. 09/098,443, Mail Date Sep. 10, 2001, Notice of Allowance.
U.S. Appl. No. 09/995,196, Mail Date Apr. 21, 2003, Office Action.
U.S. Appl. No. 09/995,196, Mail Date Aug. 27, 2003, Notice of Allowance.
U.S. Appl. No. 10/322,236, Mail Date Jun. 16, 2004, Office Action.
U.S. Appl. No. 10/322,236, Mail Date Mar. 11, 2005, Office Action.
U.S. Appl. No. 10/322,236, Mail Date Jun. 1, 2005, Office Action.
U.S. Appl. No. 10/322,236, Mail Date Jun. 23, 2005, Office Action.
U.S. Appl. No. 10/322,236, Mail Date Feb. 10, 2006, Office Action.
U.S. Appl. No. 10/322,236, Mail Date Oct. 11, 2006, Office Action.
U.S. Appl. No. 10/322,236, Mail Date Mar. 26, 2007, Office Action.
U.S. Appl. No. 10/322,236, Mail Date Jul. 30, 2007, Notice of Allowance.
U.S. Appl. No. 10/735,793, Mail Date Jan. 19, 2007, Office Action.
U.S. Appl. No. 10/735,793, Mail Date Aug. 7, 2007, Notice of Allowance.
U.S. Appl. No. 11/928,275, Mail Date Jun. 26, 2009, Office Action.
U.S. Appl. No. 11/928,275, Mail Date Jan. 13, 2010, Notice of Allowance.
U.S. Appl. No. 11/928,275, Mail Date Apr. 21, 2010, Office Action.
U.S. Appl. No. 11/928,275, Mail Date Nov. 12, 2010, Notice of Allowance.
U.S. Appl. No. 11/937,298, Mail Date Dec. 30, 2008, Office Action.
U.S. Appl. No. 11/937,298, Mail Date Jun. 29, 2009, Office Action.
U.S. Appl. No. 11/937,298, Mail Date Sep. 9, 2009, Office Action.
U.S. Appl. No. 11/937,298, Mail Date Sep. 29, 2009, Office Action.

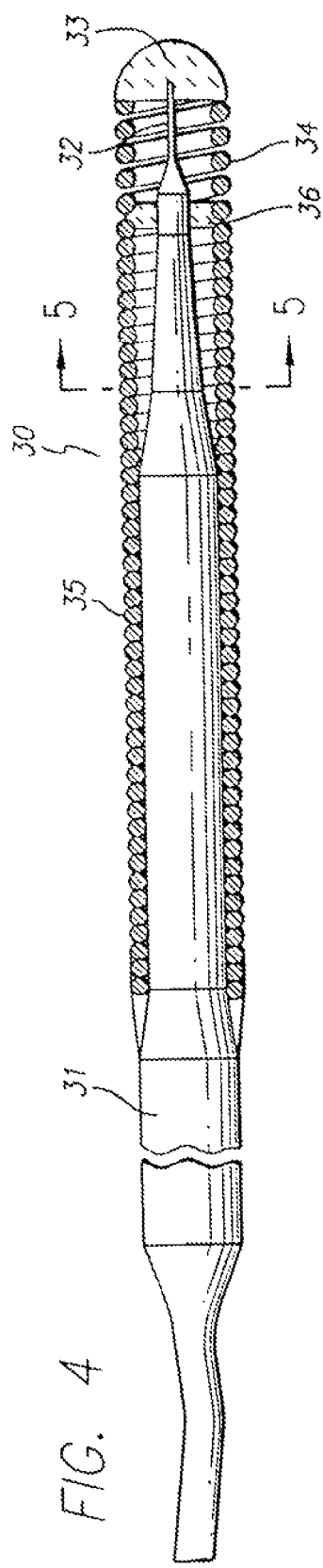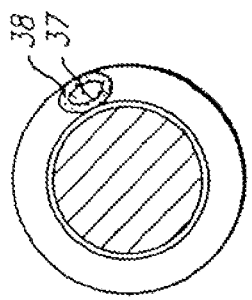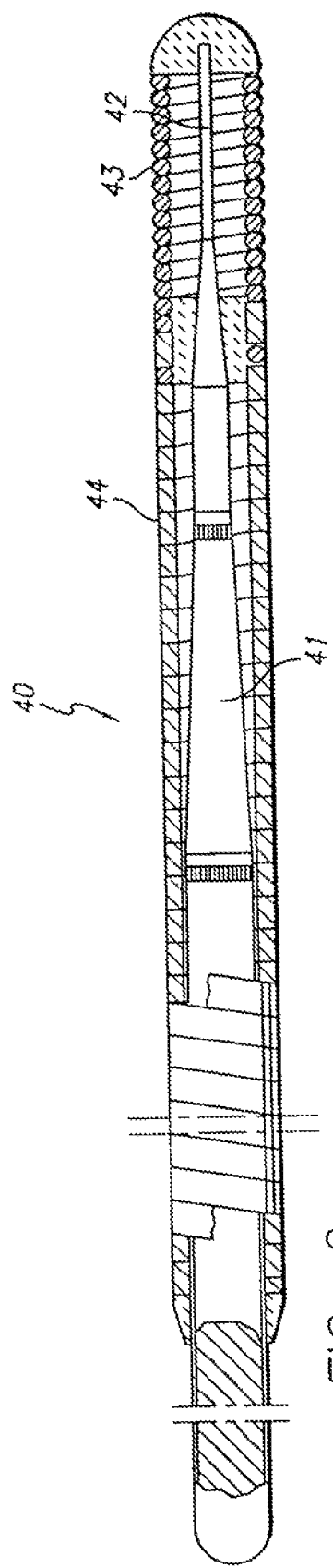

COMPOSITE RADIOPAQUE INTRACORPOREAL PRODUCT

This application is a continuation of U.S. application Ser. No. 11/928,275, filed Oct. 30, 2007, which is a continuation of U.S. application Ser. No. 10/735,793, filed Dec. 11, 2003, now U.S. Pat. No. 7,296,333, which is a divisional of U.S. application Ser. No. 09/995,196, filed Nov. 26, 2001, now U.S. Pat. No. 6,679,853, which is a continuation of U.S. application Ser. No. 09/098,443, filed Jun. 17, 1998, now U.S. Pat. No. 6,387,060, which prior applications are hereby incorporated by reference in their entirety.

BACKGROUND OF THE INVENTION

This invention relates to the field of intracorporeal medical devices such as guidewires for advancing intraluminal devices including stent delivery catheters, balloon dilatation catheters, atherectomy catheters and other intraluminal devices within a patient's body lumen.

Conventional guidewires for angioplasty, stent delivery, atherectomy and other vascular procedures usually comprise an elongated core member with one or more tapered sections near the distal end thereof and a flexible body such as a helical coil or a tubular body of polymeric material disposed about the distal portion of the core member. The flexible body may extend proximally to an intermediate portion of the guidewire. A shapable member, which may be the distal extremity of the core member or a separate shaping ribbon which is secured to the distal extremity of the core member extends through the flexible body and is secured to the distal end of the flexible body by soldering, brazing or welding which forms a rounded distal tip. Torquing means are provided on the proximal end of the core member to rotate, and thereby steer, the guidewire while it is being advanced through a patient's vascular system.

Further details of guidewires, and devices associated therewith for various interventional procedures can be found in U.S. Pat. No. 4,748,986 (Morrison et al.); U.S. Pat. No. 4,538,622 (Samson et al.): U.S. Pat. No. 5,135,503 (Abrams); U.S. Pat. No. 5,341,818 (Abrams et al.); and U.S. Pat. No. 5,345,945 (Hodgson, et al.) which are hereby incorporated herein in their entirety by reference thereto.

In a typical coronary procedure using a guidewire, a guiding catheter having a preformed distal tip is percutaneously introduced into a patient's peripheral artery, e.g. femoral or brachial artery, by means of a conventional Seldinger technique and advanced and steered therein until the distal tip of the guiding catheter is seated in the ostium of a desired coronary artery.

There are two basic techniques for advancing a guidewire into the desired location within a patient's coronary anatomy through the in-place guiding catheter. The first is a preload technique which is used primarily for over-the-wire (OTW) catheters and the second is the bare wire technique which is used primarily for rail type catheters.

With the preload technique, a guidewire is positioned within an inner lumen of an OTW device such as a dilatation catheter or stent delivery catheter with the distal tip of the guidewire just proximal to the distal tip of the catheter and then both are advanced through the guiding catheter to the distal end thereof. The guidewire is first advanced out of the distal end of the guiding catheter into the patient's coronary vasculature until the distal end of the guidewire crosses the arterial location where the interventional procedure is to be performed, e.g. a lesion to be dilated or an arterial region where a stent is to be deployed. The catheter, which is slidably mounted onto the guidewire, is advanced out of the guiding catheter into the patient's coronary anatomy over the previously introduced guidewire until the operative portion of the intravascular device, e.g. the balloon of a dilatation or a stent delivery catheter, is properly positioned across the arterial location. Once the catheter is in position with the operative means located within the desired arterial location, the interventional procedure is performed. The catheter can then be removed from the patient over the guidewire. Usually, the guidewire is left in place for a period of time after the dilatation or stent delivery procedure is completed to ensure re-access to the distal arterial location if it is necessary. For example, in the event of arterial blockage due to dissected lining collapse, a rapid exchange type perfusion balloon catheter such as described and claimed in U.S. Pat. No. 5,516,336 (McInnes et al), can be advanced over the in-place guidewire so that the balloon can be inflated to open up the arterial passageway and allow blood to perfuse through the distal section of the catheter to a distal location until the dissection is reattached to the arterial wall by natural healing.

With the bare wire technique, the guidewire is first advanced by itself through the guiding catheter until the distal tip of the guidewire extends beyond the arterial location where the procedure is to be performed. Then a rapid exchange type catheter, such as described in U.S. Pat. No. 5,061,273 (Yock) and the previously discussed McInnes et al. patent, which are incorporated herein by reference, is mounted onto the proximal portion of the guidewire which extends out of the proximal end of the guiding catheter and which is outside of the patient. The catheter is advanced over the guidewire, while the position of the guidewire is fixed, until the operative means on the rapid exchange type catheter is disposed within the arterial location where the procedure is to be performed. After the procedure the intravascular device may be withdrawn from the patient over the guidewire or the guidewire advanced further within the coronary anatomy for an additional procedure.

An important attribute for guidewires is having sufficient radiopacity to be visualized under a fluoroscope, allowing the surgeon to advance the guidewire to a desired intraluminal location, particularly the distal extremity of the guidewire. Unfortunately, the most suitable materials for guidewires, such as stainless steel and NiTi alloys, exhibit relatively low radiopacity. Accordingly, various strategies have been employed to overcome this deficiency. Portions of the guidewire, usually the shapeable distal tip, are typically made from or coated with highly radiopaque metals such as platinum, iridium, gold or alloys thereof. For example, a 3 to 30 cm platinum tip-coil is frequently soldered to the distal extremity of the guidewire. An obvious drawback of these prior art methods is the high expense and scarcity of highly radiopaque metals and the difficulty and expense of manufacturing products from these materials. The requirement of both a high degree of radiopacity, high strength and flexibility can present design problems.

Accordingly, there remains a need for guidewires having sufficient radiopacity to allow visualization under a fluoroscope without the extensive use of expensive radiopaque metals such as platinum, gold, iridium and the like.

INVENTION SUMMARY

The present invention is directed to an intracorporeal device such as a guidewire having an elongate core member with a proximal core section and a distal core section and a flexible body such as a helical coil formed of metallic wire which is disposed about and secured to at least a portion of the distal core section.

In accordance with the invention, the intracorporeal product has a body with multi-components, at least one highly radiopaque component and at least one high strength component having less radiopacity than the highly radiopaque component. The amount of the highly radiopaque component and the high strength component of the flexible body depends upon the radiopacity of each of the components. Generally, however, the highly radiopaque component should be at least about 10% but not be more than about 60%, preferably about 20% to about 40%, of the total transverse cross-section of the flexible body. The greater radiopacity the high strength component has, lessens the amount of the expensive highly radiopaque material which is needed.

The highly radiopaque material of the coil may be selected from the group of platinum, gold, iridium, highly radiopaque alloys thereof. The presently preferred highly radiopaque material is an alloy of 90% (wt) PI and 10% (wt.) Ir. The high strength material of the coil may be selected from the groups consisting of radiopaque materials such as tantalum, tungsten and silver and non-radiopaque materials such as stainless steel, NiTi alloys and Co—Cr—Mo alloys. Tantalum and alloys thereof are preferred because these materials have significant radiopacity in addition to being high strength and can more significantly reduce the amount of expensive radiopaque material which much be used for a particular degree of radiopacity. For example, a solid wire of 90% platinum—10% iridium will provide complete radiopacity, whereas, a wire of the same thickness with 70% tantalum core and 30% of a 90% Pt—10% Ir alloy cladding will provided the same degree of radiopacity but substantially improved mechanical properties. The use of non-radiopaque high strength metals will provide a fair radiopacity with adequate or improved mechanical properties depending upon the material used. A thickness of about 5 to about 10 micrometers of highly radiopaque material will usually provide complete radiopacity for intracorporeal use with conventional fluoroscopic observation.

The presently preferred form of the flexible body which is secured to the distal core section is a two component metallic wire member such as a helical coil. Other forms include a multi-wire braid formed of two-component metallic wires. In one presently preferred embodiment, the two-component wire is made of a highly radiopaque cladding and a relatively high strength material. In this way, the radiopaque material of the cladding can be chosen for its radiopaque properties and the core material can be chosen for strength properties that enhance the guidewire's performance. Alternatively, the core material may be highly radiopaque and the cladding may be formed of the high strength material.

The distal end of the helical coil may attached directly or indirectly to the distal end of the core member and it may also be secured to the core member at one or more proximal locations.

In order to increase the flexibility of the distal section of the guidewire, the core member of the guidewire may be formed in a conventional manner with a distal section having at least one tapered segment, wherein the elongate core member tapers distally to reduced transverse dimensions. If desired, the one or more distally tapered segments of the distal section of the elongate core member may be marked with radiopaque markers to indicate where a tapered segment begins or ends. In this way, a physician using the guidewire is able to identify the relative flexibility and stiffness of an area of interest on the guidewire using fluoroscopic imaging.

A second or proximal coil formed of helically shaped wire may be provided proximal to the radiopaque first coil which is formed of less radiopaque material. The wire forming the second coil may have a circular transverse cross-section or a substantially rectangular cross section. A coil of wire having a rectangular cross section provides increased stiffness and coil integrity as compared to wire with a round cross section of similar thickness, due to the increased cross sectional area. The proximal end of the second coil is attached to the distal section of the elongate core member by means of adhesive, solder and the like. The distal end of the second coil is preferably secured to the distal section of the core member by the same mass of solder or the like that secures the proximal end of the first, highly radiopaque coil to the core member.

The flexible body of the present invention has at least adequate radiopacity and strength while being substantially cheaper to make than similar structures with helical coils formed of precious metal such as platinum and gold. By appropriately choosing the materials, properties can be obtained which are better than conventional products, while significantly reducing costs.

These and other advantages of the invention will become more apparent from the following detailed description of the invention when taken in conjunction with the accompanying exemplary drawings.

BRIEF DESCRIPTION OF THE DRAWINGS

FIG. 4 is an elevational view partially in section of an alternative guidewire wherein the distal tip of the core member is flatten and extends and is secured to the distal end of the coil.

FIG. 5 is a transverse cross-sectional view of the guidewire shown in FIG. 4 taken along the lines 5-5.

FIG. 6 is a longitudinal cross-sectional view of an alternative guidewire design which has a proximal coil with a rectangular transverse cross-section.

DETAILED DESCRIPTION OF THE PREFERRED EMBODIMENTS

Figure 1:
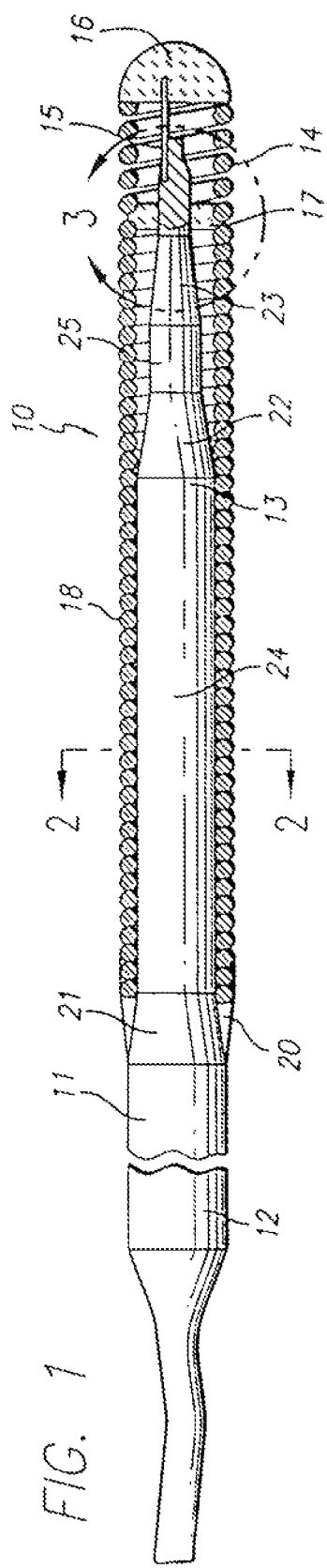
FIG. 1 is a schematic elevational view, partially in section, of a guidewire which embodies features of the invention.
Figure 3:
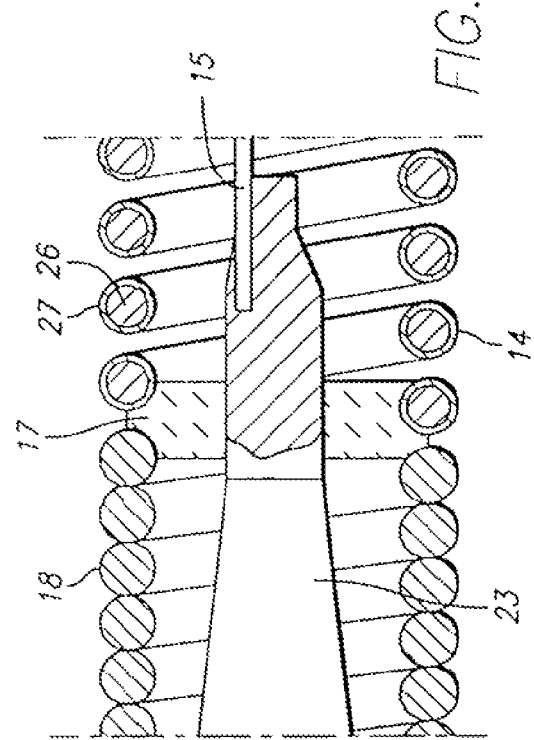
FIG. 3 is an enlarged longitudinal cross-sectional view of the guidewire shown in FIG. 1 within the circle 3.
Figure 2:
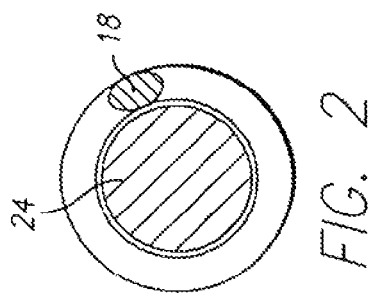
FIG. 2 is a transverse cross-sectional view of the guidewire shown in FIG. 1 taken along the lines 2-2.

FIGS. 1-3 illustrate a guidewire 10 having features of this invention that generally include an elongated core member 11, with a proximal core section 12 and a distal core section 13 and a distal, highly radiopaque helical coil 14 disposed about and secured to the distal extremity of the core member. A shaping ribbon 15 extends from the distal end of the core member 11 and is secured to the mass of solder or weldment forming the rounded distal tip 16 of the guidewire. The proximal end of the shaping ribbon 15 is secured to the distal end of the core member 11 by suitable means such as solder, brazement, weldment or adhesive. The proximal end of the distal highly radiopaque coil 14 is secured to the core member 11 by mass 17 which may be solder, brazement, weldment or adhesive. A second or proximal coil 18 is secured by its distal end to the core member by the same mass that secures the proximal end of the distal highly radiopaque coil 14 to the core member 11. The proximal end of the proximal coil 18 is secure to the core member by solder, brazement, weldment or adhesive 20. The proximal end of the distal coil 14 and the distal end of the proximal coil 18 are preferably threaded together at the site 17 of securing these ends to the core member 11.

The core member 11 of the guidewire 10, as shown in FIG. 1, generally may have conventional features with conventional dimensions. The proximal core section has a relatively constant or uniform transverse cross-sectional dimensions and the distal core section 13 has a first taper 21, a second taper 22 and a third taper 23 which taper in the distal direction to smaller transverse cross-sectional dimensions. An first intermediate uniform dimensioned core portion 24 extends between the first and second tapers 21 and 22 and a second intermediate uniform dimensioned core portion 25 extends between the second taper 22 and the third taper 23.

As shown in more detail in FIG. 3, the distal highly radiopaque coil 14 has an inner portion 26 and an exterior portion 27. The inner portion or core 26 of coil 14 is formed of high strength metallic material such as stainless steel, NiTi alloy, Co—Cr—Mo alloys such as Elgiloy or MP35N and tantalum (or alloys thereof). Tantalum is presently preferred because it also has a high degree of radiopacity in addition to high strength. The exterior portion or cladding 27 is formed of a highly radiopaque metallic material such as platinum, gold, iridium, palladium, tantalum, tungsten, silver and highly radiopaque alloys thereof. If desired these components forming the wire of coil 14 may be reversed, i.e. the inner portion 26 may be highly radiopaque and the cladding 27 may be formed of high strength material.

FIG. 4 illustrates a guidewire 30 which has various alternative embodiments. The first alternative embodiment is the core member 31 having a flattened distal extremity 32 (instead of a shaping ribbon) which extends and is secured to the rounded mass 33 of solder, brazement, weldment or adhesive which is secures the distal end of the distal, highly radiopaque coil 34 thereto. The proximal helical coil 35 may be formed of conventional stainless steel wire. As in the embodiment shown in FIGS. 1 and 3 the distal end of the second proximal coil 35 is secured to the core member 31 at the same location 36 as the proximal end of the distal, highly radiopaque coil 34. The distal, highly radiopaque coil 34, as shown in FIG. 5 is formed of an inner component 37 of highly radiopaque material and an outer component 38 of high strength material.

Another alternative design is depicted in FIG. 6. In this design, the guidewire 40 has a core member 41 with a flattened distal extremity 42 as in the embodiment shown in FIG. 4. While not shown in detail the distal coil 43 has a highly radiopaque cladding and a high strength core as described for the embodiment of FIGS. 1-3. However, the proximal coil 44 disposed about the core member 41 has an essentially rectangular shaped transverse cross-section as compared to the circular transverse cross-section of the distal coil 43. The rectangular transverse cross-section provides additional support. This guidewire design is primarily for peripheral arteries and generally has larger dimensions than the embodiments shown in FIGS. 1-5.

Another alternative design is depicted in FIG. 6 In this design, the guidewire 40 has a core member 41 with a flattened distal extremity 42 as in the embodiment shown in FIG. 4. While not shown in detail the distal coil 43 has a highly radiopaque cladding and a high strength core as described for the embodiment of FIGS. 1-3. However, the proximal coil 44 disposed about the core member 41 has an essentially rectangular shaped transverse cross-section as compared to the circular transverse cross-section of the distal coil 43. The rectangular transverse cross-section provides additional support. This guidewire design is primarily for peripheral arteries and generally has larger dimensions than the embodiments shown in FIGS. 1-5.

The clad wire forming the distal coil may be formed in a variety of ways. The presently preferred manner is to prepare a tubular member of one of the components and a solid core (e.g. wire or rod) of the other component suitably sized so that the tubular member formed of one component can be co-drawn with the solid core of the other component to flow with the latter to form a strong bond. It is presently preferred to form the tubular member of the highly radiopaque material and the core member of the high strength material with a lesser radiopacity. Other means for forming the clad wire for the distal coil include plasma spraying one component onto a wire or rod of the other component. Physical vapor deposition may also be employed in a similar manner. Electroplating and other more conventional methods may be used to form the clad product.

Generally, the overall length of the guidewire may range from about 80 to about 320 cm, preferably about 160 to about 200 for coronary use. Typically, commercial guidewire products of the invention will come in standard lengths of 175, 190 and 300 cm. The distal section of the guidewire is about 1 to about 10 cm, preferably about 2 to about 5 cm in length, the intermediate section is about 15 to about 50, preferably about 25 to about 40 cm in length. The outer diameter of the guidewire may vary depending upon use, but typically is about 0.008 to about 0.035 inch (0.2-0.9 mm). The lengths and diameters of the tapers may likewise vary. The composite wire forming the proximal and distal coils will typically have a diameter of about 0.002 to about 0.006 inch (0.051-0.15 mm). A 0.002 inch diameter composite wire is typically used for forming a coil of about 0.010 to about 0.014 inch (0.25-0.36 mm) in diameter, a 0.0025 inch (0.063 mm) wire for a coil with an OD of 0.0014 inch and a wire of 0.0055 inch (0.14 mm) for larger OD coils. To the extent not otherwise described herein, the dimensions, constructions and materials of the guidewire may be conventional.

Although individual features of embodiments of the invention may be shown in some of the drawings and not in others, those skilled in the art will recognize that individual features of one embodiment of the invention can be combined with any or all the features of another embodiment. Various modification may be made to the invention without departing from the scope thereof.

We claim:

1. An intracorporeal medical device, comprising:
   a flexible body defining a lumen extending therethrough, the flexible body including, an interior core; and
   a radiopaque cladding that is about 10% to no more than 60% of a cross-sectional area of the flexible body.

2. The intracorporeal medical device of claim 1, wherein the flexible body comprises a wire that is at least partially coiled.

3. The intracorporeal medical device of claim 1, wherein the flexible body forms part of a guidewire.

4. The intracorporeal medical device of claim 1, wherein the radiopaque cladding is about 20% to about 40% of the cross-sectional area of the flexible body.

5. The intracorporeal medical device of claim 1, wherein the flexible body is formed by co-drawing a wire comprising an exterior of a first radiopacity and a core of a second radiopacity, wherein the first radiopacity is greater than the second radiopacity.

6. The intracorporeal medical device of claim 1, wherein the radiopaque cladding is deposited onto the high strength interior core.

7. The intracorporeal medical device of claim 1, wherein the radiopaque cladding is deposited onto the high strength interior core by at least one of electroplating, plasma spraying, or physical vapor deposition.

8. The intracorporeal medical device of claim 1, wherein the flexible body exhibits substantially the same radiopacity as platinum-based wire made from 90 weight % platinum and 10 weight % iridium and having the same thickness as the flexible body.

9. The intracorporeal medical device of claim 1, wherein the interior core includes at least one material selected from the group consisting of a nickel-titanium alloy, a Co—Cr—Mo alloy, tantalum, a tantalum alloy, tungsten, and a tungsten alloy, and wherein the radiopaque cladding includes at least one material selected from the group consisting of platinum, gold, iridium, palladium, tantalum, tungsten, silver, and alloys thereof.

* * * * *